(12) United States Patent
Nagel et al.

(10) Patent No.: US 7,148,010 B2
(45) Date of Patent: Dec. 12, 2006

(54) METHOD FOR DETECTING POLYNUCLEOTIDE SEQUENCES

(76) Inventors: Michael Nagel, Hospitalstrasse 113, 41571, Viersen (DE); Peter Haring Bolivar, Turmstrasse 19, 4730, Raeren (BE); Heinrich Kurz, Rote-Haag-Weg 1b, 52076, Aachen (DE); Martin Brucherseifer, Pontwall 12, 52072, Aachen (DE); Katrin Bosserhoff, Elsenborn 68a, 52072, Aachen (DE); Reinhard Büttner, Rue du Vivier 22, 4851, Gemmernich (BE)

( * ) Notice: Subject to any disclaimer, the term of this patent is extended or adjusted under 35 U.S.C. 154(b) by 514 days.

(21) Appl. No.: 10/332,780

(22) PCT Filed: Jun. 29, 2001

(86) PCT No.: PCT/DE01/02408

§ 371 (c)(1),
(2), (4) Date: Aug. 5, 2003

(87) PCT Pub. No.: WO02/04928

PCT Pub. Date: Jan. 17, 2002

(65) Prior Publication Data

US 2004/0058339 A1    Mar. 25, 2004

(30) Foreign Application Priority Data

Jul. 10, 2000 (DE) ............................. 100 33 258
Nov. 3, 2000 (DE) ............................. 100 54 476

(51) Int. Cl.
C12Q 1/68 (2006.01)
G01N 15/06 (2006.01)
G01N 33/00 (2006.01)
C07H 21/04 (2006.01)

(52) U.S. Cl. .............. 435/6; 422/68.1; 536/23.1; 536/24.3

(58) Field of Classification Search ............ 435/6; 536/23.1, 24.3; 422/68.1
See application file for complete search history.

(56) References Cited

U.S. PATENT DOCUMENTS 5,485,277 A    1/1996  Foster
6,242,246 B1   6/2001  Gold et al.

FOREIGN PATENT DOCUMENTS

WO    WO-99/39008 A1    8/1999
WO    WO-00/50867 A2    8/2000

OTHER PUBLICATIONS

Markelz, A.G. et al, "Pulsed terahertz spectroscopy of DNA..." Chem. Phys. Lett. 320 (2000) 42-48.
Hunsche, S. et al, "THz near-field imaging", Optics Communications 150 (1998) 22-26.
Brucherseifer, M. et al. "Label-free probing of..." Appl. Phys. Lett. 77, No. 24 (2000) 4049-4051.
Migdall, A. et al. "Terahertz spectral measurements..." Am. Phys. Soc. Mar. 1999 Meeting abstract.
Gallerano, G.P., "Far Infrared and Terahertz Effects..." Workshop abstract—FZR Rossendorf, 1999.

*Primary Examiner*—Jezia Riley
(74) *Attorney, Agent, or Firm*—Akerman Senterfitt

(57) ABSTRACT

The invention relates to a method for proving the existence of a polynucleotide sequence A in a sample containing a plurality of identical or different polynucleotide sequences X as individual strands and where the polynucleotide sequence A may be identical with one of the polynucleotide sequences X or may be contained as a sequence portion in one of the polynucleotide sequences X, through the inquiry of the state of linkage of the polynucleotide sequences X contained in the sample to a known test polynucleotide sequence B complementary to the polynucleotide sequence A, comprising the following steps: preparation of a test medium containing as individual strands test polynucleotide sequences B complementary to the polynucleotide sequence A which is to be proven, establishing contact of the sample with the test medium by placing the sample into or onto the test medium such that the individual strands of the polynucleotide sequences X contained in the sample may bind to the complementary test polynucleotide sequences B contained in the test medium. For proving a linkage of polynucleotide sequences X to test polynucleotide sequences B, the following step c) is carried out: determination of at least one component of the complex index of refraction or of a parameter equivalent to it of the sample which is in contact with the test medium by interaction with incident electro-magnetic radiation, the frequency of which is within the range of 0.1 terahertz (THz) and 20 THz, preferably between 1 THz and 10 THz and subsequent analysis of the properties of the electro-magnetic radiation after the interaction, in particular in respect of time delay or phase delay, absorption, refraction or dispersion of the incident electro-magnetic radiation caused by the interaction.

9 Claims, 6 Drawing Sheets

Figure 1:
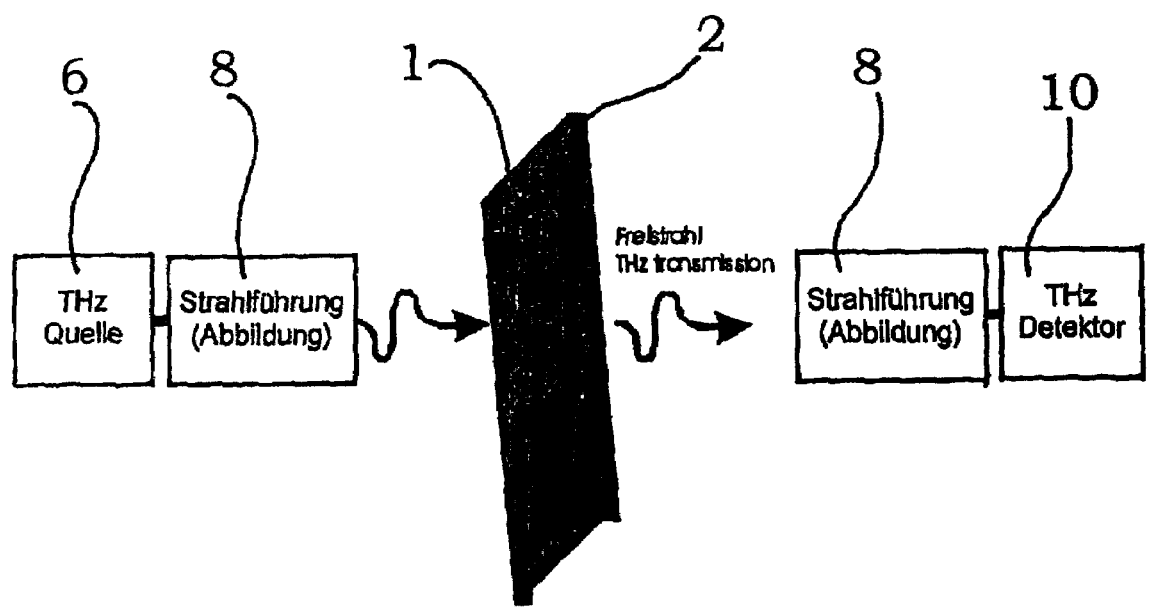

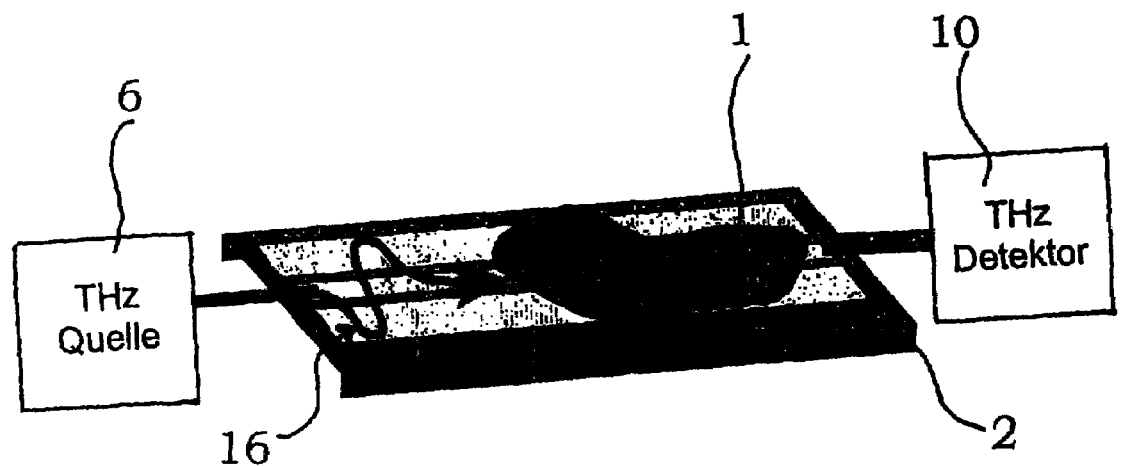
Fig. 4
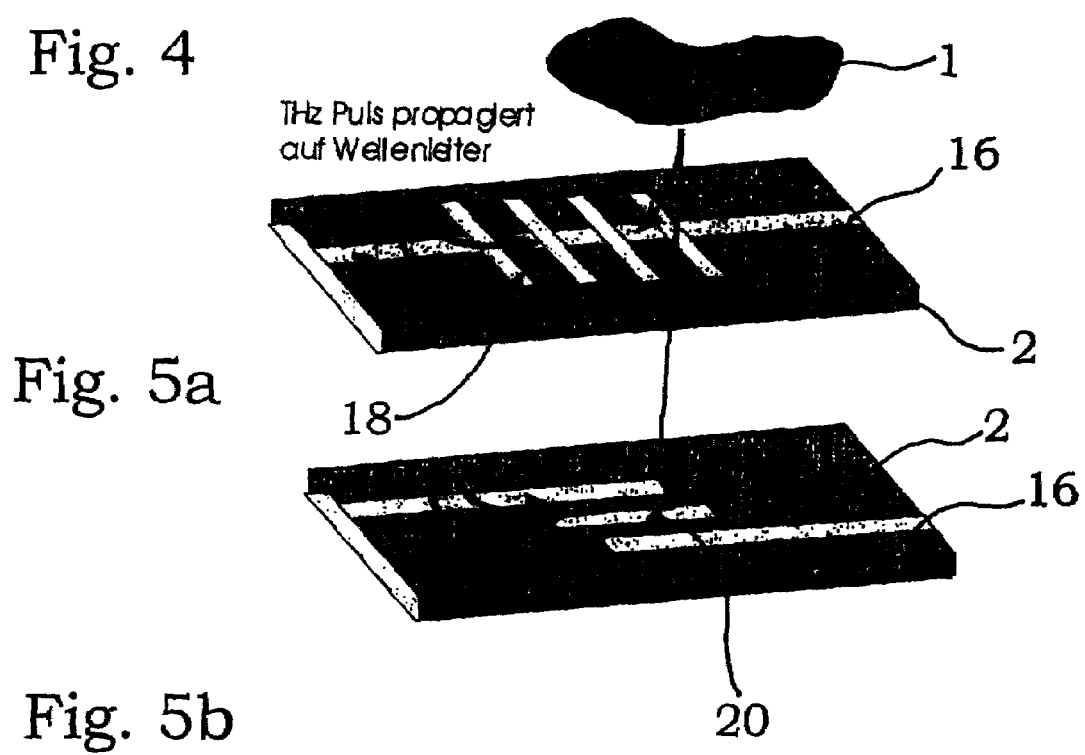
Fig. 5a
Fig. 5b

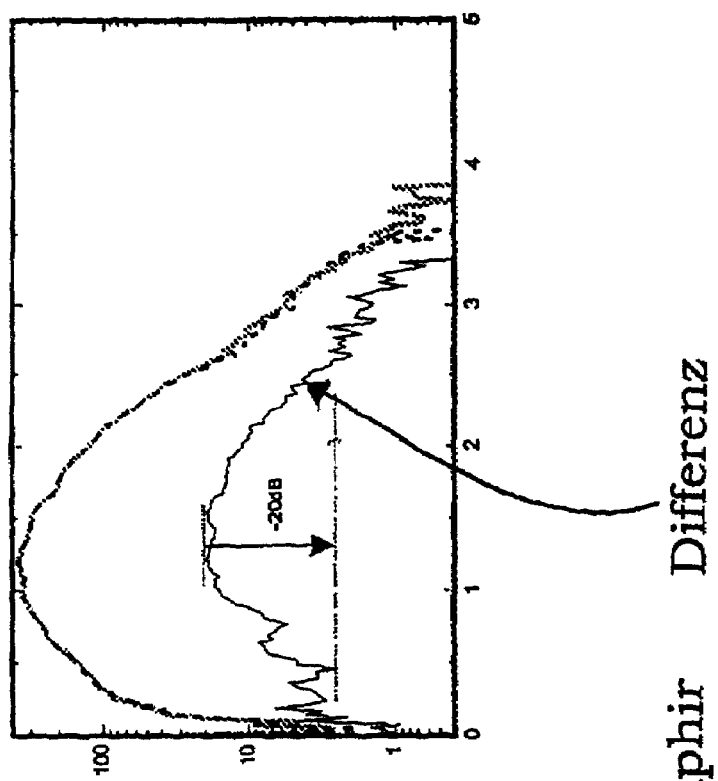
Fig. 7b Differenz
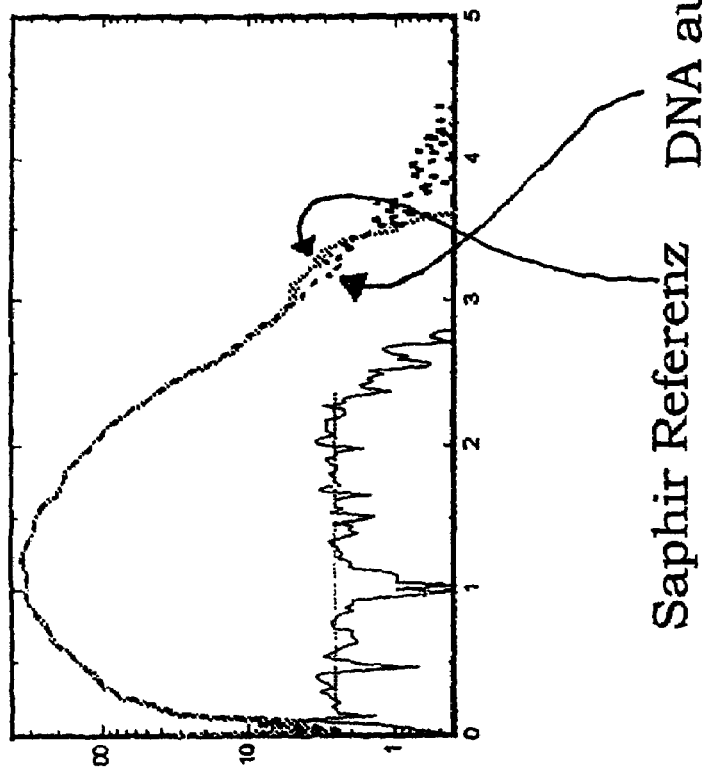
Fig. 7a Saphir Referenz  DNA auf Saphir

METHOD FOR DETECTING POLYNUCLEOTIDE SEQUENCES

The present invention relates to a method for proving the existence of a polynucleotide sequence in a sample containing a plurality of identical or different polynucleotide sequences in the form of individual strands with the characteristics of the preamble of the Main Claim. Such methods are used for the determination of specific polynucleotide sequences, for instance from DNA from the sample of a patient.

Relevant methods for determining specific polynucleotide sequences are known from the state of art. The method which is generic-determining in this case is based on the use of a test polynucleotide sequence which is complementary to the polynucleotide sequence the existence of which is to be proven. When the polynucleotide sequences which are complementary to each other and are present in the form of individual strands come into contact, they link with each other forming a double strand. Since the linkage between the individual strands is essentially generated by means of hydrogen bridge linkages, the energies of the respective linkages between the individual strands are within the range of milli-electron volt. By means of appropriate detection methods it is being checked whether a polynucleotide sequence contained in the sample has linked to the test polynucleotide sequences or not.

The detection methods known from the state of the art which are based on this principle of detection comprise essentially the following sequence of steps:

a) preparation of a sample, for instance a sample from a patient which contains a plurality of identical or different polynucleotide sequences, here termed X, in the form of individual strands. This sample may contain the polynucleotide sequence the existence of which is to be proven, here termed A. In this, the polynucleotide sequence A the existence of which is to be proven may be identical with one of the polynucleotide sequences X which are contained in the sample or may be contained as a component in such a polynucleotide sequence X.

b) Preparation of a test medium which contains in the form of individual strands test polynucleotide sequences which are complimentary to the polynucleotide sequence A the existence of which is to be proven. In general, these test polynucleotide sequences, hereinafter referred to as B, are fixed on a substrate.

c) The sample is brought into contact with the test medium, for instance by dripping the sample which is available in the form of a solution onto the substrate on which the complementary test polynucleotide sequences B are fixed. When suitable conditions prevail, the polynucleotide sequences A which may be contained in the sample and which are to be detected bind to the complementary test polynucleotide sequences B which are fixed on the substrate. Such a linkage between the complementary polynucleotide sequences A and B is possible when the polynucleotide sequence A is contained in an identical form in the sample and also when the polynucleotide sequence A is contained in the sample as a component of a longer-chain polynucleotide sequence X.

d) In a detection step that follows now, it is being checked whether polynucleotide sequences A and B linked to form a double strand A-B are contained in the sample which is in contact with the test medium. When a substrate is used on which the test polynucleotide sequences B are fixed, the effect is exploited that these paired complementary polynucleotide sequences A and B are present on the surface of the substrate in a considerably increased concentration. In order to prove the existence of the polynucleotide sequences A-B which are paired to form a double strand, several detection methods are known from the state of the art.

Detection methods are widely used which are based on marking the polynucleotide sequence A that is to be detected or the test polynucleotide sequence B which is complementary to it with fluorescent colours. If polynucleotide sequences marked in such a manner are available in a diluted form, for instance as a solution, only a weak fluorescence is observed with an appropriate lighting of the solution. If the marked polynucleotide sequence gets, however, concentrated in the region of a boundary surface, for instance due to an addition reaction with a complementary polynucleotide sequence which is fixed on a substrate, then the density of the fluorescent molecules increases there locally by several orders of magnitude. When proper lighting exists, those areas of the substrate to which the polynucleotide sequence A that is to be detected has become increasingly attached to the substrate, to be more precise, to the complementary test polynucleotide sequence B which is fixed thereon, present themselves, therefore, as a distinctly detectable fluorescent area of the surface. By means of a quantitative determination of the fluorescence, for instance by means of taking a photographic picture of the brightness of the fluorescent areas, a quantitative determination of the polynucleotide sequences A that are to be detected and which are bound to the complementary test polynucleotide sequences B is possible.

In the meantime, the respective methods have attained a high level in their development. The spaced separate arrangement of different known complementary test polynucleotide sequences B, B' . . . in the form of an array on a substrate permits now the simultaneous detection of a plurality of different polynucleotide sequences A, A' . . . in one sample. Relevant methods are, for instance, known from [Chena96] and [Chee96].

The marking of the polynucleotide sequences with fluorescent colours has, however, a number of considerable disadvantages. On the one hand, it involves an additional expenditure for marking either the polynucleotide sequences A which are to be detected or the test polynucleotide sequences B that are complementary to them with suitable fluorescent colours. In order to be able to carry out the relevant marking, bio-chemical methods are required which, on the one hand, must be developed involving great expenditure and which, on the other hand, involve another preparation step in large-scale application which causes still greater expenses. Furthermore, it is known from studies that the marking with fluorescent colours of polynucleotide sequences which are present in the form of individual strands may result in conformation changes of the polynucleotide strand. Such conformation changes may, in spite of a complete complementarity of two single-strand polynucleotide sequences, lead to a reduced probability of linkage between both individual strands since the conformation of the individual strands is of essential importance for the linkage probability. Relevant results are, for instance, known from [Osaki 92].

Moreover, it is known that the marking with fluorescent colours has a negative impact on the quantifiability of the results. The reason for that is, for instance, that the intensity of the fluorescence of the fluorescent colours depends to a great extent upon the linkage site at which the fluorescent colours are linked with the single-strand polynucleotide sequence. Furthermore, subsequent processing steps may entail fluctuations of the efficiency of the marking process. Relevant results were presented by [Zhu94], [Zhu97] and [Laramendi98].

For these reasons, it would be desirable to find a detection method that can be used, within the framework of the generic method, for proving the existence of nucleotide sequences A and B which are linked with each other in the form of a double-strand which does not require any additional preparatory steps and which has no negative impact on obtaining quantitative results.

An approach which is rather physically oriented when compared to the marking with fluorescent colours is the analysis of existing single-strand or paired polynucleotide sequences A and B which are attached to a boundary surface, by means of spectroscopic methods. It was, for instance, proposed to use the method of the Forier Transformation Infrared Spectroscopy (in short: FTIR) for the differentiation between polynucleotide sequences which exist as single-strand and double-strand polynucleotide sequences. The results showed, however, only a weak dependence upon the really relevant issue, that is whether the complementary polynucleotide sequences A and B were present in the form of individual strands or in the form of pairs. To date, it cannot be established that, by using the FTIR method, a reliable and quantitative proof of the state of linkage of a polynucleotide sequence A which is to be detected to a complementary polynucleotide sequence B would become possible.

This is where the present invention comes in. The object of the invention is to further develop the generic method in such a way that the marking of the polynucleotide sequence A which is to be detected or of the polynucleotide sequence B which is complementary to it, for instance by means of fluorescent colours, can be dispensed with. At the same time, in comparison with the already known method which is based on the use of an FTIR based detection method of the state of linkage of the polynucleotide sequences A and B, a distinctly increased sensitivity is to be attained which permits the detection of the state of linkage between the complementary polynucleotide sequences A and B.

The generic proving method is in particular intended for the quantitative determination of the concentration of the polynucleotide sequence A in the sample.

The aforesaid object is achieved by a method with the elements specified in the Main Claim.

Consequently, this is a method for proving the existence of a polynucleotide sequence A in a sample which contains the polynucleotide sequence A in the sample (also) in form of individual strands. The sample contains a plurality of identical or different polynucleotide sequences X (also) in the form of individual strands. The polynucleotide sequence A to be proven can be identical with one of the polynucleotide sequences X or can be contained as a sequence portion in one of the polynucleotide sequences X.

The proving method is based on the linkage of the polynucleotide sequence A to a known test polynucleotide sequence B complementary to the polynucleotide sequence A, and on an inquiry of the state of linkage of the polynucleotide sequences X and the test polynucleotide sequence B. The method comprises the following steps:

a) preparation of a test medium containing as individual strands test polynucleotide sequences B complementary to the polynucleotide sequence A which is to be proven, b) establishing contact of the sample with the test medium by placing the sample into or onto the test medium such that the individual strands of the polynucleotide sequences X contained in the sample can bind to the complementary test polynucleotide sequences B contained in the test medium. A linkage between a specific polynucleotide sequence X and the test polynucleotide sequence B will essentially occur when the polynucleotide sequence X is identical with the polynucleotide sequence A to be proven or contains the polynucleotide sequence A to be proven as a sequence portion. A linkage will occur due to the complementarity of the polynucleotide sequences A and B.

c) inquiry of the state of linkage of the polynucleotide sequences X to polynucleotide sequences B by determination of at least one component of the complex index of refraction or of a parameter equivalent to it of the sample which is in contact with the test medium. This is achieved by interaction with the sample which is in contact with the test medium, with incident electro-magnetic radiation, the frequency of which is within the range of 0.1 terahertz (THz) and 20 THz, preferably between 1 THz and 10 THz. After the interaction of the incident electro-magnetic radiation with the sample which is in contact with the test medium the properties of the electro-magnetic radiation after the interaction will be analysed, in particular in respect of time delay or phase delay, absorption, refraction or dispersion of the incident electro-magnetic radiation caused by the interaction with the sample which is in contact with the test medium.

As a linkage between a polynucleotide sequence X and the test polynucleotide sequence B occurs essentially only if the test polynucleotide sequence X is identical with the polynucleotide sequence A to be proven or contains it in an identical form, the proof of a linkage of polynucleotide sequences X to the test polynucleotide sequence B proves that the sample contains the polynucleotide sequence A to be proven, either in an identical form or as portion of a long-chain polynucleotide sequence X.

The method according to the invention therefore comprises a step c) which serves to prove the state of linkage of the test polynucleotide sequence B, i.e. for the inquiry of whether the test polynucleotide sequence exists in denatured or in hybridised form. Step c) is based on the interaction of the sample which is in contact with the test medium with electro-magnetic radiation in the terahertz range and the determination of at least one component of the complex index of refraction or of a parameter equivalent to it, e.g. absorption, transmission or reflection, of the sample which is in contact with the test medium.

In a first embodiment of the method according to the invention, the component of the complex index of refraction or the parameter equivalent to it as determined in step d) are compared with a reference value in a subsequent step. Based on the comparison with the reference value, at least a qualitative, but very often so a quantitative statement is possible regarding the existence of a linkage between polynucleotide sequences X and the test polynucleotide sequence B.

In the context of pre-tests it has proved useful to consider the real part of the complex index of refraction of the sample which is in contact with the test medium as the parameter that characterises the state of linkage. Upon the transition of the polynucleotide sequence A to be proven from the individual strand given in the sample and the complementary test polynucleotide sequence B contained in the test medium in the form of an individual strand, to an interconnected double strand A-B, the index of refraction of the sample which is in contact with the test medium changes in the THz range which can be dissolved consistently by means of experimental methods known from the state of the art. Therefore the real part of the index of refraction can be used as proof for the existence of a linkage between the polynucleotide sequence A to be proven and the complementary test polynucleotide sequences B. This can be achieved in particular by comparison with a reference value, e.g. one referring to unpaired test polynucleotide sequences B.

A number of theoretical works deals with the excitation states of double-strand polynucleotide sequences, see also [Zhuang90], [Young90] and [Feng 91]. These works predict a variety of possible excitation states of individual and double-strand polynucleotide sequences, e.g. in the form of vibration modes, etc. A variety of possible excitation states occur only in the moment when two single-strand polynucleotide sequences bind to a double strand. It is also possible that certain excitation states of the single strands do not occur any more or are strongly suppressed, once they bind to a double strand. The energy ranges where the excitation of the separate single strands occurs is clearly different from the energy range where excitation states occur which are caused by the existence of a double-strand polynucleotide sequence.

Despite of these statements laid down in previous theoretical works, a concrete statement as to the energy range where these excitations that are typical for the existence of a double-strand polynucleotide sequence occur cannot yet be made at the moment. Surprisingly it turned out in the context of experimental tests that the inquiry of the state of linkage of two complementary single-strand polynucleotide sequences A and B in the frequency interval specified in the Main Claim is possible with a high efficiency.

Based on the theoretical works on the excitation states of paired polynucleotide sequences, the hypothesis can be put forward that by means of the determination of at least one component of the complex index of refraction within the frequency interval specified in the Main Claim exactly those excitation states of the double-strand polynucleotide sequence are inquired which are essentially caused by the double-strand conformation of the polynucleotide sequence. It should therefore be possible to optimise the detection method according to the invention in that at least one component of the complex index of refraction of the sample which is in contact with the test medium in such a frequency range where excitation states of either the denatured, i.e. double-strand polynucleotide sequence, or of the single-strand polynucleotide sequence occur, which is essentially caused by the double-strand or single-strand structure, is determined.

Particular benefits of the application of the method according to the invention become evident when at least one component of the complex index of refraction or of a parameter equivalent to it is determined according to step c) of the Main Claim by means of Terahertz Spectroscopy (TS).

In the context of pre-tests it has proved particularly beneficial to use pulsed radiation for the Terahertz Spectroscopy, i.e. the determination is carried out by means of pulsed Terahertz Spectroscopy (PTS). Particular benefits can be achieved with terahertz pulses with a pulse duration between 0.05 picoseconds and 10 picoseconds. In order to determine at least one component of the complex index of refraction or of a parameter equivalent to it by means of PTS, the pulses are being detected in time resolution after having interacted with the sample which is in contact with the test medium. The techniques required for pulsed Terahertz Spectroscopy are known from the state of the art. The basic techniques and methods are specified, for example, in [Smith 88], [Nuss 98] and [Haring 99]. Further information on time resolution PTS can be found in [Wittlin 95].

The required pulsed electro-magnetic radiation within the frequency interval specified in the Main Claim with a pulse duration appropriate for the execution of time resolution measurements can be generated, for example, by means of photoconductive switches constructed in semiconductor technology. In order to generate the pulses in the terahertz range, these photoconductive switches are exposed to radiation by means of ultra-short laser pulses, whose duration is in the range of some 10 femtoseconds and whose wavelength is typically in the range of the near infrared, in this case in particular between 700 and 900 nanometres. The underlying mechanisms can be found for example in [Katzenellenbogen 92]. In particular in order to improve the radiation characteristics of the terahertz radiation, appropriate antennas can be used which are arranged near the photoconductive switch to improve the radiation properties of the THz source.

The basic structure of a system for the execution of a time resolution PTS is specified e.g. in [Cai 98].

The time resolution PTS is basically carried out as follows:
1. Generation of pulsed electro-magnetic radiation with a frequency in the terahertz range and a typical pulse duration of 0.5 to 5 picoseconds. In particular pulses with a frequency range of approx. 1 to 5 gigahertz are being used.
2. The pulsed terahertz radiation is lead to the sample by means of appropriate ray guides.
3. The pulsed terahertz radiation is brought to interaction with the sample to be tested which is in contact with the test medium.
4. After the interaction with the sample the pulsed terahertz radiation is guided to a detector by means of appropriate ray guides.
5. The incident pulsed terahertz radiation which has interacted with the sample is analysed in the detector. In particular, the time history of the pulses incident in the detector is determined in time resolution. This determination in time resolution is carried out preferably relative to terahertz pulses which were not in interaction with the sample.

Two different methods are known for the time resolution determination of terahertz pulses after the interaction with the sample. One method is based on the change of the optical properties of an electro-optical crystal when transmitted by the terahertz pulse. Such changes of the optical properties of the electro-optical crystal are inquired in time resolution by means of a shorter pulse—in terms of time—in the range of the visible spectrum or the near infrared, particularly by means of femtosecond pulses in the near infrared.

In an alternative approach, the changes of the conductivity of a photoconductive switch—again constructed in semiconductor technology, as a consequence of the incident terahertz pulses are inquired in time resolution merely electronically. Both methods are equivalent to each other and can be used alternatively in the context of the method required here. Details on the second method can be found, for example, in [Dahl 1998].

By means of the appropriate Fourier transformation methods, the intensity history of the terahertz pulses, for example, which have interacted with the sample can be determined from the time history as a function of frequency. The (frequency-related) transmission of the terahertz pulses through the sample can be directly determined by comparing the intensity history of a pulse which has interacted with the sample, with the intensity history of a reference pulse which has not interacted with the sample. Thus the transmission through a sample to be tested can be compared with the transmission through a sample which does reliably not contain any molecules of the polynucleotide A to be proven. A potential reduction or increase of the intensity of the terahertz pulses transmitting through the sample, relative to the reference, can therefore be reguarded as a direct proof of whether the polynucleotide sequences X contained in the sample which is in contact with the test medium, exist still in a single-strand form in the presence of the test polynucleotide sequences B, i.e. they are hybridised, or whether at least a part of them linked to the test polynucleotide sequences B forming double strands, i.e. they occur in a denatured form now. A potential change of intensity is a measure for the absorption occurring in the sample which is in contact with the test medium, and is therefore equivalent to the imaginary part of the complex index of refraction of the sample which is in contact with the test medium.

Alternatively to the determination of the absorption, i.e. of the imaginary part of the complex index of refraction, it is also possible to determine the real part of the imaginary index of refraction of the sample which is in contact with the test medium, in particular so a change of the real part of the complex index of refraction. Such change of the real part of the complex index of refraction can also be used as a proof of whether the polynucleotides X contained in the sample occur essentially in hybridised or denatured form after the contact of the sample with the test medium was established. Further details are shown in the embodiments.

Alternative to the application of the pulsed Terahertz Spectroscopy PTS, in this case preferably in time resolution, the determination of at least one component of the complex index of refraction or of a parameter equivalent to it according to step c) of the method according to the invention can also be carried out by means of an interaction of the sample with a narrow-band terahertz radiation that is detected in frequency resolution. Particular possibilities are, for example, transmission measurements of continuous and quasi-continuous, i.e. narrow-band, terahertz radiation through the sample which is in contact with the test medium. Furthermore, the real part of the complex index of refraction of the sample which is in contact with the test medium can be directly determined by means of diffraction measurements. Finally, all applicable methods known from the state of the art can be used to determine at least one component of the complex index of refraction or of a parameter equivalent by means of narrow-band terahertz radiation.

If the narrow-band terahertz radiation used is detected in frequency resolution, it is possible to apply scattering methods known from optics such as the Raman scattering and the Brillouin scattering of molecules in the terahertz range. The components of the complex index of refraction or the parameters equivalent to them can also be determined by appropriate scattering tests within the frequency interval specified in the Main Claim.

In order to carry out the method according to the invention using the pulsed Terahertz Spectroscopy PTS several possibilities are imaginable to make the sample to be tested which is in contact with the test medium interact with the pulsed terahertz radiation.

In a first embodiment of the method according to the invention, the pulsed terahertz radiation generated by an appropriate THz source propagates freely until it is brought to interaction with the sample which is in contact with the test medium. After the interaction, the pulsed terahertz radiation again propagates freely until it reaches a THz detector. This method is referred to as "free-ray arrangement" in the following.

Alternatively, a so-called "near-field arrangement" can be established. This arrangement is based on the knowledge, that a particular high-intensity terahertz radiation required for the method according to the invention can be achieved in the near field of special appropriate near-field emitters. In a further embodiment of the method according to the invention, the required terahertz radiation is therefore generated by means of a near-field emitter directly next to the sample which is in contact with the test medium. After the interaction of the terahertz radiation with the sample which is in contact with the test medium the terahertz radiation can be guided to an appropriate detector by means of conventional ray-guiding methods.

Alternatively, a complementary arrangement is possible where the terahertz radiation is generated by means of a conventional terahertz emitter and is guided by means of conventional ray-guides guides, e.g. metallic mirrors, to the sample which is in contact with the test medium. After the interaction of the terahertz radiation with the sample which is in contact with the test medium the terahertz radiation can be detected and analysed by means of an appropriate terahertz near-field detector.

Both embodiments of near-field arrangements have the benefit that a high local resolution can be achieved which is particularly useful if the hybridised or denatured polynucleotide sequences to be proven are located on a substrate, particularly so if the test polynucleotide sequence B is fixed on a substrate. Analogous to the Array proving methods for the simultaneous analysis of a sample for different polynucleotide sequences A, A' . . . (in) a substrate which are known from the state of the art, the sample can be tested simultaneously for the existence of a plurality of different polynucleotide sequences A on the basis of the available local information.

In a further preferable embodiment of the method according to the invention, the terahertz radiation required for spectroscopy propagates before, during or after the interaction with the sample which is in contact with the test medium on or within a wave-guide. This ensures a highly efficient ray guidance. Furthermore, appropriate miniature apparatuses can be constructed for the execution of the method by means of structuring methods known, e.g. from the area of the semiconductor technology.

Finally, particular advantages can be achieved during the performance of the method according to the invention, if the wave-guide structure within the area of the sample which is in contact with the test medium is such that due to the modified properties of the terahertz radiation in this area an increased sensitivity of the method according to the invention is achieved. The wave-guide structure within the area of the sample which is in contact with the test medium can in particular be provided with a resonator structure or a frequency filter which locally intensify the field strength of the terahertz radiation. It is also possible to influence the properties of the wave guides to make them frequency-related, i.e. with the help of the appropriate wave-guide structures, e.g. by means of a frequency filter. This allows, for example, the generation of a sharp edge in the frequency-related transmission by the wave-guide structure, which can be influenced by at least one component of the complex index of refraction or of a parameter equivalent to it of the sample which is in contact with the test medium. In particular, a displacement of the frequency edge may occur, for example, through a modification of the complex index of refraction, e.g. by modifying the absorption.

Analogous to the detection methods known from the state of the art for polynucleotide sequences, which are based on marking the polynucleotide sequence A that is to be detected with fluorescent colours, it has proven particularly beneficial for the performance of the method according to the invention to fix the complementary polynucleotide sequences B contained in the test medium on or in a substrate. This allows to achieve a high concentration of the denatured polynucleotide sequences A to be proven on the surface where the complementary test polynucleotide sequences B are fixed. Such increased concentration at the interface is useful especially in connection with surface-sensitive or interface-sensitive detection methods for the existence of denatured polynucleotide sequences performed in accordance with the method according to the invention.

In a further improved embodiment of the method according to the invention in step b) the polynucleotide sequences X which are contained in the sample but which are not bound to the complementary polynucleotide sequences B are removed before the determination of at least one component of the complex index of refraction or the parameter equivalent to it. This can be done, in particular, by washing out the test medium that is in contact with the sample. This additional step avoids problems which can be caused if the sample itself does not only contain the single-strand polynucleotide sequence A, but also the complementary polynucleotide sequence B in form of individual strands. Such simultaneous existence of the complementary polynucleotide sequences A and B can be caused, for example, by previous steps carried out to hybridise the polynucleotide sequences X contained in the sample and a subsequent insufficient separation of the individual strands.

The test medium is preferably washed out in a way ensuring that the polynucleotide sequences X contained in the sample, which are preferably bound to the complementary polynucleotide sequences B fixed on a substrate, keep sticking, while the rest of the sample is removed.

In a further preferable embodiment of the method according to the invention a plurality N of different polynucleotide sequences A (1) . . . , A (N) is proved simultaneously in the sample. To this end, a plurality N of test media is being prepared, which respectively contain a test polynucleotide sequence B[1], . . . , B[N] complementary to the polynucleotide sequences A(1), . . . , A(N). The test media are fixed at different sites on or in a substrate. Now at least one component of the complex index of refraction or of a parameter equivalent to it is determined according to steps b) and c) for each individual test medium that is in contact with the sample. This can be achieved by means of local-resolution detection methods. In particular the interaction with focussed terahertz radiation or terahertz near-field emitter or near-field prober can be used here.

Figure 2:
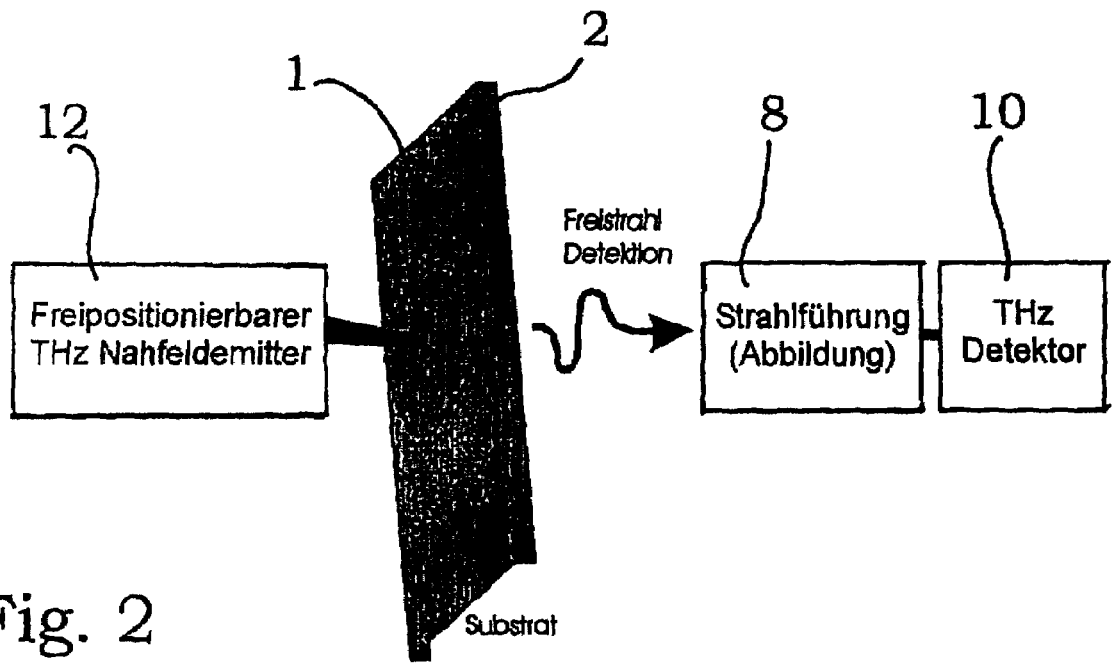
Figure 3:
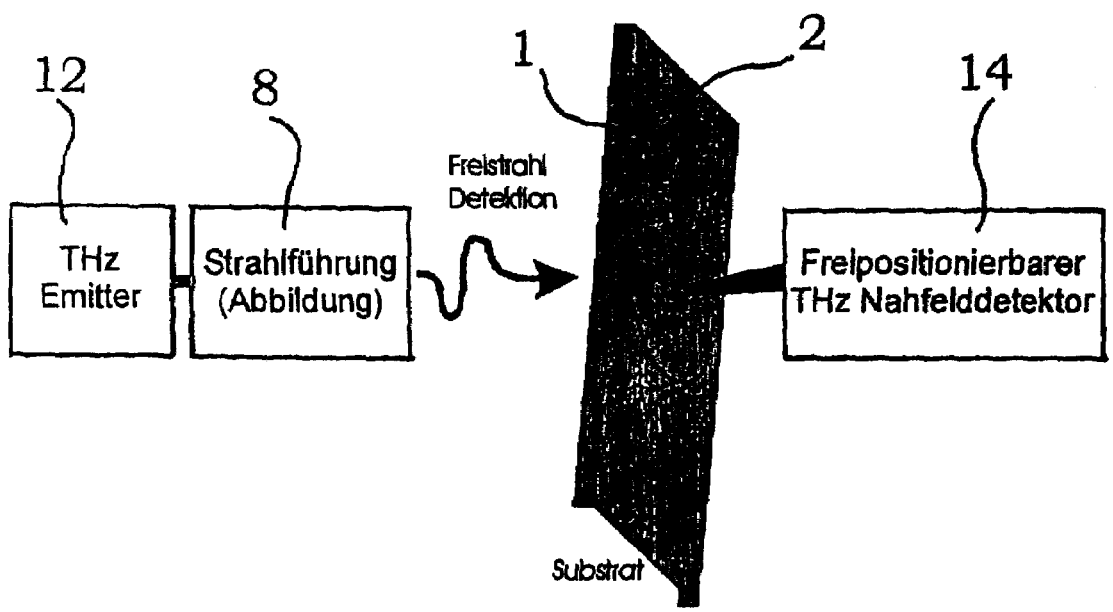
Figure 6:
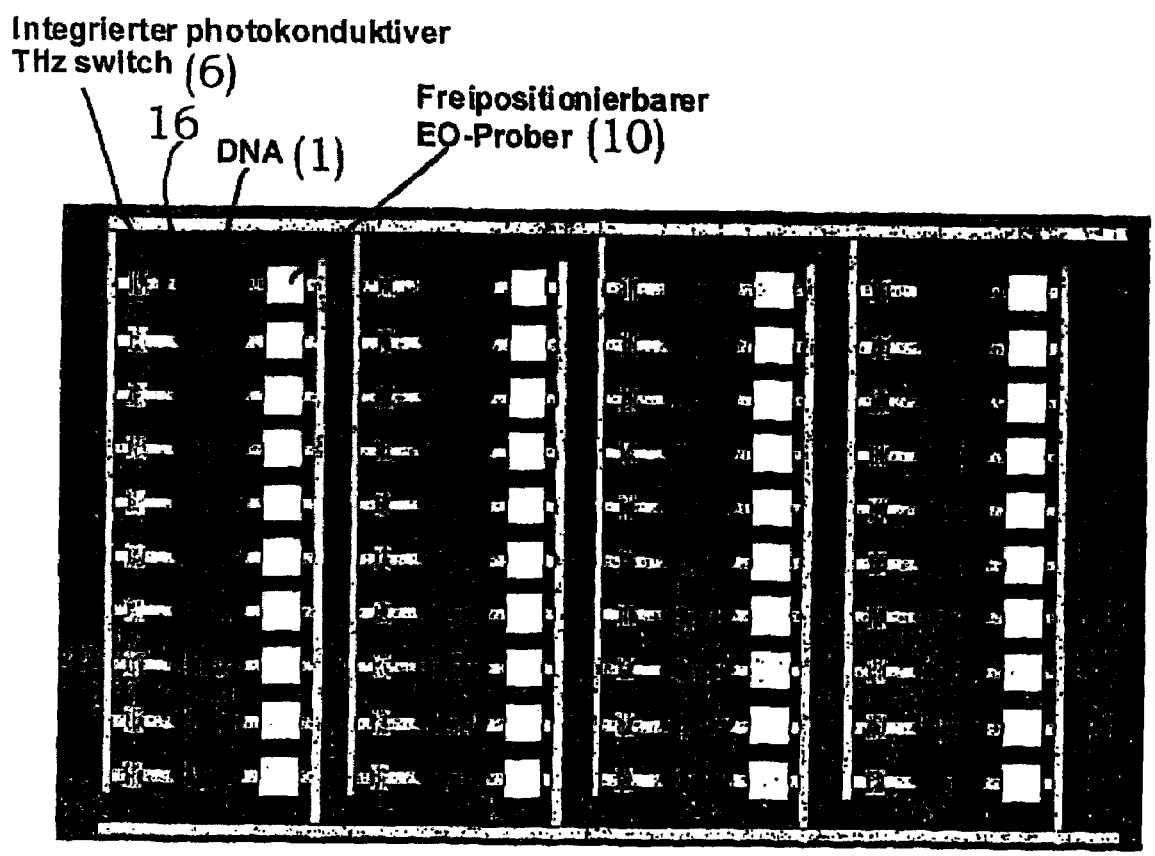
Figure 8:
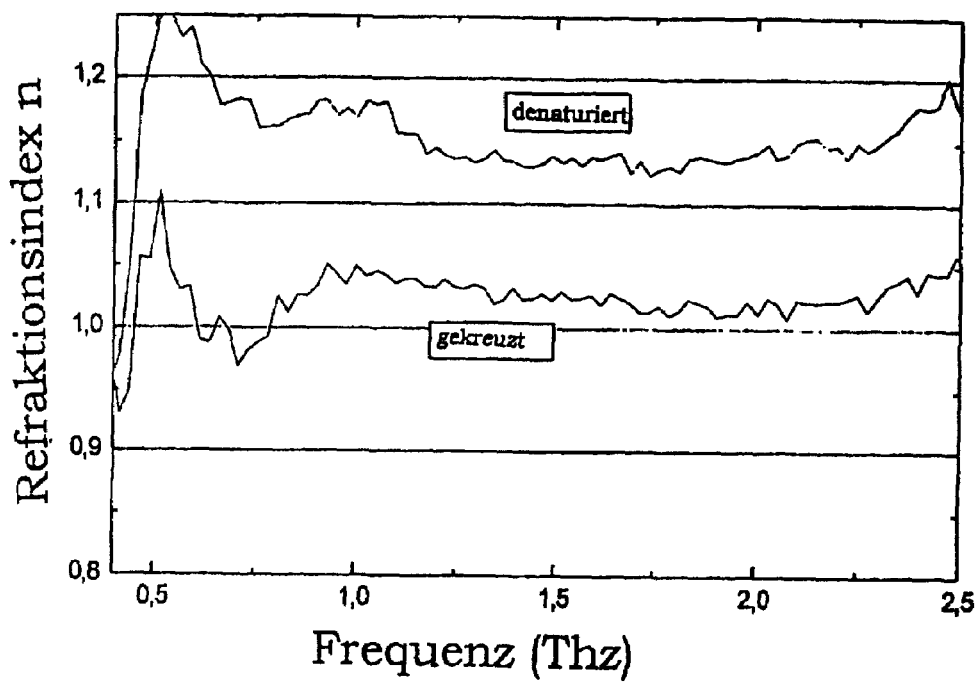
Figure 9:
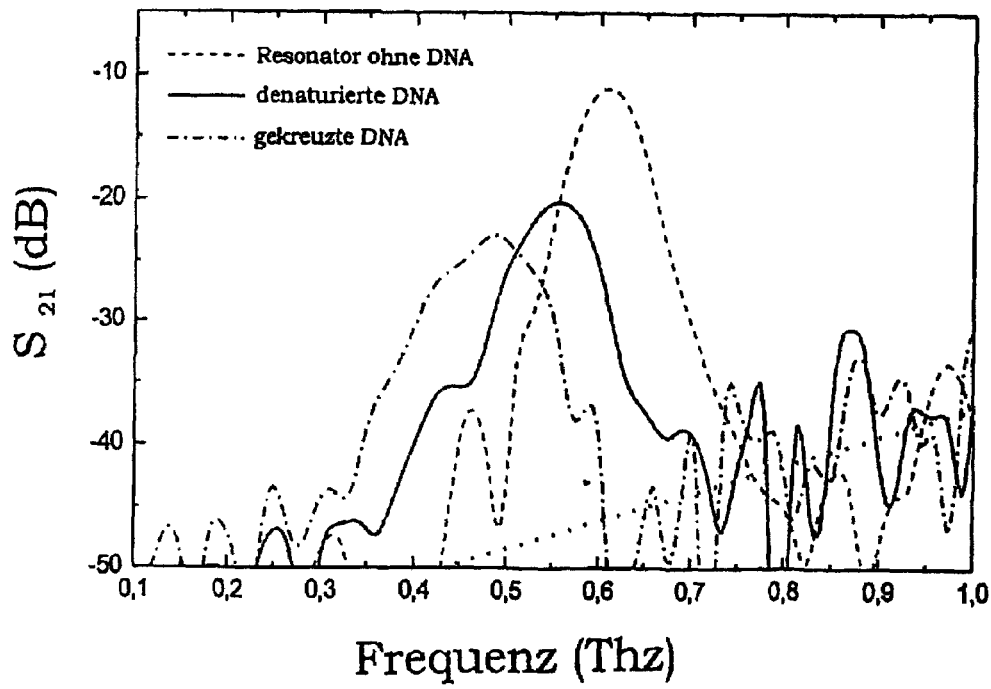

Further advantages and features of the method according to the invention are specified in the sub-claims as well as in the following embodiments—but not limited to them—and which will be explained with reference to the figures. The figures depict in detail:

FIG. 1: a schematic illustration of an apparatus for the execution of the method according to the invention in a free ray arrangement, FIG. 2: a schematic illustration of an apparatus for the execution of the method according to the invention in a first near-field arrangement, FIG. 3: a schematic illustration of an apparatus for the execution of the method according to the invention in a second near-field arrangement, FIG. 4: a schematic illustration of another apparatus for the execution of the method according to the invention comprising a wave-guide for the terahertz radiation, FIG. 5a: an apparatus in accordance with FIG. 4, providing a resonator structure integrated in the wave-guide, FIG. 5b: an apparatus in accordance with FIG. 4, providing a filter structure integrated in the wave-guide, FIG. 6: a two-dimensional array of wave-guide structures, e.g. in accordance with FIG. 4, FIG. 7a: results of a transmission measurement by means of time resolution Terahertz Spectroscopy by a sample containing a polynucleotide sequence to be proven in denatured form, FIG. 7b: results of a transmission measurement by a sample containing a polynucleotide sequence to be proven in hybridised form, FIG. 8: the frequency-related route of a real part of the complex index of refraction of a sample containing a polynucleotide sequence to be proven in hybridised or denatured form, and FIG. 9: the results of a transmission measurement through a planar wave-guide structure.

FIG. 1 depicts a first arrangement for the execution of the method according to the invention. Sample 1 used in a hydrous solution containing different single-strand, i.e. denatured polynucleotide sequences X in dissolved form. It shall be proven whether sample 1 contains a certain single-strand polynucleotide sequence A. Where A is either identical with one of the polynucleotide sequences X or is contained in it in identical form, i.e. either

X=A or

X=YZAVZ where V, Y, Z can be any other polynucleotide sequences.

Sample 1 is located on the surface of a substrate 2 consisting of a sapphire lamina of a strength of approx. 1 mm. Fixed upon the substrate surface 2 are single-strand test polynucleotide sequences B which are complementary to the polynucleotide sequence A to be proven. Substrate 2 forms together with the test polynucleotide sequences B fixed on it the test medium 4.

The polynucleotide sequences X contained in the hydrous solution in sample 1 arrive at the surface of substrate 2 and thus at the test polynucleotide sequences B fixed on it. If one of the polynucleotide sequences X is identical with A or if A is contained in X in identical form, this polynucleotide sequence X can bind to a test polynucleotide sequence B, i.e. in connection with B it can form a hybridised (i.e. double-strand) polynucleotide sequence X-B. Because a linkage between X and B occurs only if A is identical with X or if A is contained in X as a sequence portion, this shows that the polynucleotide sequence A to be proven exists in hybridised form in sample 1 which is in contact with the test medium 4. Because B is fixed on the surface of substrate 4 the double-strand polynucleotide sequence X-B is also fixed on the surface. Therefore the concentration of the single-strand polynucleotide sequences X which contains the required polynucleotide sequence A or is identical to it is gradually reduced in the test solution, whereby at the same time the concentration of the double-strand polynucleotide sequences X-B at the surface of the substrate is increased. Compared to sample 1, a high concentration of A is reached on the substrate surface.

By means of the appropriate methods and electro-magnetic radiation of a frequency range between 0.1 THz and 20 THz at least one component of the complex index of refraction or of a parameter equivalent to it of sample 1 which is in contact with the test medium 4 is now determined.

In order to minimise the influence of potential other polynucleotide sequences that may be contained in the hydrous sample 1 on the method, it may be recommendable to wash out and dry substrate 2 in a way ensuring that only the polynucleotide sequences X of the sample that are bound to the test polynucleotide sequence B remain on the substrate surface, and that the rest of sample 1 including the solvent, i.e. the water, is removed. A thin film consisting essentially only of double-strand polynucleotide sequences X-B and potential water storages is formed on the substrate surface.

By means of a THz source 6 a broad-band pulsed electro-magnetic radiation is generated, the frequency of which is in the frequency interval between 0.1 THz and 20 THZ. The typical pulse duration is between 0.01 picoseconds (ps) and 10 ps, the pulse repetition rates are in the range of several 10 to 100 MHz.

The pulsed THz radiation is guided by appropriate ray-guide means 8 to substrate 2 and imaged on it. In particular the area of substrate 2 where the double-strand polynucleotide sequences X-B have concentrated on the substrate surface in the case that the required polynucleotide sequence A was contained in sample 1 is exposed to radiation. Metallic concentrating reflectors can be used, for example, as ray guides.

Sample 1 which is in contact with the test medium 4, in this case the said section of the substrate surface, in particular either the denatured test polynucleotide sequences B or the hybridised double-strand polynucleotide sequences X-B contained in it, is exposed to the THz radiation and interacts with it. This causes modifications of the incident THz radiation which allows to draw conclusions regarding the presence or absence of double-strand polynucleotide sequences X-B and hence the presence of the polynucleotide sequence A to be proven in sample 1.

After the interaction with sample 1 which is in contact with test medium 4 the THz radiation which transmitted through substrate 2 is guided by appropriate ray-guides 8 from sample 1 to a THz detector 10 and is analysed there. FIG. 1 depicts a free-ray arrangement for the execution of the method according to the invention, where the THz radiation propagates freely before and after the interaction with sample 1 which is in contact with test medium 4.

An alternative arrangement is depicted in FIG. 2. With sample 1 being arranged in the same way on substrate 2, the THz radiation is generated close to the substrate surface, in particular close to the section where the test polynucleotide sequences B are fixed, by means of a THz near-field emitter 12 that is freely positionable in relation to the substrate surface. Such THz near-field emitter 12 can be, for example, a miniature THz source constructed in semiconductor technology which can be combined, in particular, with a THz antenna for a directed THz radiation. A THz source 6 with dimensions clearly below the wavelength of the THz radiation, i.e. a so-called THz near-field emitter 12, can be constructed, for example, by means of the technology known from the near-field optical microscopy. Reference is made here to the high number of publications on the subject "scanning near-field optical microscopy" (abbr.: SNOM).

In principle, the objective in near-field optics, also when applying optical detection methods, is to achieve a resolution capacity below the wavelength of the light used. This can be achieved by means of special optical near-field emitters which reach a concentration of radiated intensity in a ray beam with a diameter of at least one order of magnitude below the wavelength of the emitted radiation in their optical near field which extends to only some 10 nanometres from the emission surface of the near-field emitter. When a near-field emitter is placed near the sample at such a distance that the sample is located in the near field of the near-field emitter this allows a local high-resolution inquiry of optical properties of the sample.

If within the scope of the method according to the invention a THz near-field emitter 12 is used analogously, the "THz-optical" properties of sample 1 to be examined can be determined in the same way with a high local resolution. In particular, the complex index of refraction of sample 1, or at least one component of it or of a parameter equivalent to it, can be inquired with a high local resolution.

The THz radiation emitted by the THz near-field emitter 12 impinges sample 1 which is in contact with test medium 4 and interacts with it. After the interaction with sample 1 the transmitted THz radiation is guided again by appropriate ray-guides 8 to a THz detector 10 and is detected by it.

Hence, compared to the arrangement depicted in FIG. 1 the arrangement shown in FIG. 2 allows to achieve a clearly increased spatial resolution which provides advantages when miniaturising the apparatus required for the execution of the method according to the invention as well as for the simultaneous execution of the method on a high number of samples 1 or with a high number of test media 4.

A comparably high resolution also is provided by the apparatus designed for the execution of the method which is depicted in FIG. 3. The generation and ray guidance of the THz radiation to sample 1 as well as the interaction of the THz radiation with the sample are equivalent to FIG. 1. But the THz radiation having transmitted through sample 1 which is in contact with the test medium 4 is now detected by means of a freely positionable THz near-field emitter 14 with a high local resolution. THz near-field emitter 14 has the same "near-field optical" properties as near-field emitter 12 depicted in FIG. 2 and is arranged in the near field of the sample.

FIG. 4 depicts an alternative approach for the execution of the method according to the invention. Substrate 4, on which sample 1 was applied by dropping, provides an integrated wave-guide structure 16 for the THz radiation, along which the THz radiation can propagate. Sample 1 is applied to the surface of the wave-guide structure 16. Due to the fact that the field of the THz radiation extends beyond the wave-guide structure 16 vertically to its surface in form of an evanescent wave, the THz radiation propagating along wave-guide 16 can interact with sample 1 at least in the area close to the surface of the wave-guide structure 16. In fact, the field strength of the evanescent wave on the surface of the wave-guide structure 16 is even increased compared to the THz radiation that propagates freely in space.

After the interaction of the THz radiation with sample 1 to be examined the THz radiation that transmitted along the wave-guide structure is detected by an appropriate THz detector 10. This detector can either be designed for freely propagating radiation analogous to THz detector 10 depicted in FIG. 1, or alternatively, it can be integrated, for example, in the wave-guide structure 16 in semiconductor technology.

FIG. 5a depicts a wave-guide structure 16 with an integrated additional resonator structure 18 which is resonant for the THz radiation used. In the range of resonator structure 18 the field strength of the THz radiation propagating in the wave-guide structure is heavily increased. If sample 1 is applied to the wave-guide in the range of resonator structure 18, this will increase the field strength of the evanescent wave again resulting in an increased sensitivity of the arrangement due to an improved signal-to-noise ratio.

FIG. 5b depicts another wave-guide structure with an integrated frequency-selective element 20, e.g. a short-fit filter for the THz radiation that propagates along the wave-guide structure. The frequency-selective element provides with respect to its transmissivity for THz radiation at least a sharp cutting edge. The exact location of the cutting edge is determined by the properties of the frequency-selective element 20 and can also depend strongly on the surface properties of the substrate, in or on which the frequency-selective element 20 is established. Modifications of the substrate surface, e.g. of the real part of the complex index of refraction of a surface-near lamina by an addition of polynucleotide sequences X to the test polynucleotide sequences B fixed to it, can result in strong changes of the properties of the frequency-selective element 20, in particular in a displacement of the cutting edge. The displacement can be used in turn to determine at least one component of the complex index of refraction or of a parameter equivalent to it of sample 1 which is in contact with the test medium 4, i.e. here a modified transmission of the THz radiation by the frequency-selective element 20.

Finally, FIG. 6 depicts a 2-d array of wave-guide structures 16 which provide the structure depicted in FIG. 4. The THz detectors 10 used are electro-optical crystals ("EO prober") whose optical properties which are influenced by the incident THz radiation are detected in time resolution by means of appropriate methods. To achieve an optimum excitation of the THz radiation radiating along the wave-guide structure 16, the EO prober can be freely positioned on the surface of substrate 2. The array depicted in FIG. 6 allows the parallel execution of the method according to the invention on a high number of samples 1 or with a high number of test media 4.

All arrangements specified above are based on the detection and analysis of transmitted THz radiation. Of course all arrangements are as well possible in reflection analogously, and also THz radiation scattered in interaction with sample 1 can be detected and analysed.

Experimental Run 1:

In a first experimental run a sample was examined for the existence of a specific (DNA-) polynucleotide sequence A in denatured or hybridised form. The vector selected as the polynucleotide sequence to be proven was vector "pcDNA3" (obtained from Invitrogen, Carlsbad, Calif., USA) with a size of 5.4 kB. The vector was amplified in *E.coli* and cleaned by means of the Nucleobond-PC500 system (obtained from Macherey-Nagel, Düren, Germany). The concentration of the (DNA-) polynucleotide sequence A, i.e. of the vector pcDNA3, was adjusted in a first sample to 17 μg/μl and in a second sample to 5 μg/μl in two times distilled water.

The (DNA-) polynucleotide sequences which existed in the sample in the form of double strands were denatured in a part of the test solution by increasing the temperature of the test solution to 95° C. for a period of 5 minutes. The denaturing process was shock-stopped by cooling down with ice in order to suppress a renaturing of the now single-strand (DNA-) polynucleotides.

In the solution where the denaturing process was stopped abruptly the polynucleotide A to be proven existed in the form of separated individual strands. In the terminology of the Main Claim this solution therefore contained simultaneously the (single-strand) polynucleotide A to be proven and the complementary test polynucleotide B in the form of the individual strands of vector pcDNA3 which were separated from each other.

In the solution where no denaturing of vector pcDNA3 had been carried out the (single-strand) polynucleotide A to be proven existed therefore, in the terminology of the Main Claim, in the form bound to the complementary test polynucleotide B in the test solution.

Therefore in both cases the test solution constituted the sample 1 within the meaning of the Main Claim which was in contact with the test medium 4.

In a first experimental run the examinations were carried out on polynucleotide samples in a free-ray arrangement. To this end, drops of the test solution with a size of 2 μl containing polynucleotides in denatured or hybridised form in a concentration of 17 μg/μl were applied on sapphire substrates and were allowed to dry for a period of 48 hours in order to reduce the residual moisture to below 1%. According to investigations carried out by [Markelz 00] the water content turned out relevant for the index of refraction of the samples in the THz range. After the drying out of the drops thin films with a diameter of approx. 2 mm and a strength of approx. 30 μm had formed.

Now transmission measurements were carried out on the prepared thin films in a dry atmosphere at 300 Kelvin. A standard structure for time resolution pulsed Terahertz Spectroscopy was used, as known, for example, from [Smith 88]. The light source used for the generation of the THz pulses was an industrial femtosecond Ti:Saphir laser system which generated pulses with a pulse duration of approx. 100 fs in the near infrared.

Alternately, at least 10 independent reference measurements on uncoated substrates and measurements on substrates coated with the sample to be tested were carried out. In order to minimise the influence of unavoidable experimental fluctuations all measurements were repeated on several different samples.

FIG. 7*a* depicts a THz transmission spectrum in frequency resolution obtained from a Fourier transformation of the pulses detected in time resolution after interaction with the samples which contained the polynucleotide sequence A to be proven, i.e. the vector pcDNA3, in denatured, i.e. single-strand form. The transmission measurements were carried out in a free-ray arrangement here under vertical incidence on the sample.

FIG. 7*b,* however, shows the THz transmission spectrum in time resolution obtained in the same experimental arrangement from the samples which contained the polynucleotide sequence A to be proven in hybridised, i.e. double-strand form.

Both, FIGS. 7*a* and 7*b,* show the curves of the transmission spectrums of the uncoated sapphire substrates (dotted line), on the one hand, and of the sapphire substrates which were coated with the thin films (dashed line), on the other hand. The thin continuous line shows the complex difference of the transmission spectrums each of the uncoated and of the coated substrate.

For both samples, the transmission spectrums of the uncoated substrate and the substrate coated with the respective sample are very similar which is due to the low thickness of the samples. The differential spectra (thin continuous line) of both samples, however, show a course that depends strongly on whether the polynucleotide sequence A, i.e. the vector pcDNA3, exists in the form of individual strands, i.e. denatured, or in the form of double strands, i.e. hybridised. The thin dotted line in FIG. 7a shows the mean value of the frequency-related complex difference between the uncoated sapphire substrate and the sapphire substrate that was coated with the sample.

In the case of the sample which contained the polynucleotide sequence A to be proven in denatured form only a small complex difference can be seen, as depicted in FIG. 7a. In contrast, in the sample containing the polynucleotide sequence A to be proven in hybridised form, the result is a clearly increased complex difference reflecting a strong dependence on the frequency. As a result of the comparison of the two complex differences the complex difference in the case of the hybridised sample is by approx. 20 dB above the complex difference of the denatured sample.

Therefore a differentiation between the hybridised and denatured polynucleotide sequence A or the complementary test polynucleotide sequence B within the meaning of the Main Claim is possible, e.g. with respect to the variation between the complex differences between a test medium 4 containing only the complementary test polynucleotide sequence B and a test medium 4 which is in contact with sample 1. If sample 1 contains the polynucleotide sequence A to be proven, A exists in hybridised form, i.e. bound to the complementary test polynucleotide sequence B. If, however, sample 1 does not contain the polynucleotide sequence A to be proven, only the denatured test polynucleotide sequence B is present. If, as specified above, the complex differences of the transmission spectra are compared with each other by test medium 4 alone on the one hand, and on the other hand by test medium 4 which is in contact with sample 1, the courses of the complex differences enable to differentiate whether the complementary test polynucleotide sequence B is present in denatured or in hybridised form. In the first case sample 1 does not contain the polynucleotide sequence to be proven, in the second case A is contained in the sample. Hence the complex difference of refraction is a parameter that is equivalent to the complex index of refraction within the meaning of the Main Claim.

Furthermore, the real part as well as the imaginary part of the complex index of refraction of the sample can be used as a proving criterion for the state of linkage of the test polynucleotide sequence B and thus for the existence of the polynucleotide sequence A to be proven in sample 1. Based on the frequency-related transmission spectra in FIGS. 7a and 7b the complex indexes of refraction of the samples can be determined directly according to the Fresnel formulas. The real part of the complex index of refraction is a parameter for the dispersion of the sample which is in contact with the test medium 4.

The bottom curve in FIG. 8 depicts the course of the real part of the complex index of refraction of the samples which contained the polynucleotide sequence A to be proven in single-strand, i.e. in denatured form. The top curve in FIG. 8, however, depicts the course of the real part of the complex index of refraction of the samples which contained the polynucleotide sequence A to be proven in double-strand, i.e. in hybridised form. Both curves can be clearly differentiated from each other as they provide a difference of approx. $\Delta n \geq 0,1$ in the frequency interval shown. Hence it is possible to prove the existence of the required polynucleotide sequence A in the sample 1 by means of a determination of the difference between the real parts of the complex indexes of refraction of two samples of which one sample contains only the test polynucleotide sequence B which therefore exists in denatured form, and the other contains the test polynucleotide sequence B which is in contact with sample 1, and contains therefore the test polynucleotide sequence B in hybridised form, if the polynucleotide sequence A to be proven is contained in sample 1.

Analogous statements can also be made with respect to the imaginary part of the complex index of refraction of sample 1 which is in contact with the test medium 4, characterising the absorption in the sample. This, however, is not demonstrated here explicitly. It turned out that the real part of the complex index of refraction has a lower sensitivity for pollution and that therefore inter alia an increased exactness of the method according to the invention can be achieved when the real part of the complex index of refraction of the sample is used as a proving criterion.

The fact that the sample which contains the polynucleotide sequence to be proven in hybridised form provides a clearly increased index of refraction, implies in correspondence with the previous theoretical works of [Saxena 89] and [Zhuang 90] quoted above that there are excitation states existing in double-strand polynucleotide sequences whose excitation energies are in the frequency range of THz radiation specified in the Main Claim, whereas these excitation states do not exist in single-strand polynucleotide sequences or are strongly suppressed there. An inquiry of these excitation states is therefore an appropriate means of differentiation between denatured or hybridised polynucleotide sequences, in particular the test polynucleotide sequence B, in the scope of the method according to the invention.

Reference is made to the fact that also a mere measurement of the absorption in the frequency interval specified in the Main Claim provides a possibility to determine at least one component of the complex index of refraction or of a parameter equivalent to it of the sample 1 which is in contact with the test medium 4, because the absorption occurring in the sample is directly linked with the imaginary part of the complex index of refraction.

Experimental Run 2:

In a second experimental run the samples were not examined in a free-ray arrangement, but in a wave-guide arrangement. Here the fact of the modification of the transmission characteristics of a resonator integrated in a wave-guide structure due to the modification of the dielectric properties of a coating on the resonator was used.

To this end, a planar wave-guide structure with an integrated resonator with a resonance frequency of approx. 600 GHz was established. FIG. 9 depicts the frequency-related course of the parameter $S_{21}$ characterising the transmission through the resonator in the frequency interval between 0.1 and 1 THz. The thin dashed line shows the course for an uncovered resonator.

If a drop of the test solution is applied to the planar wave-guide structure in the area of the resonator and is allowed to dry out there, the surface of the resonator will be coated with a thin layer of dielectric material, i.e. with the polynucleotide sequences A (pcDNA3) contained in the test solution either in denatured or in hybridised form. This dielectric coating modifies the transmission characteristics of the resonator.

The thick continuous curve in FIG. 9 depicts the course of $S_{21}$ for a coating consisting of a dried-out sample (concentration: 5 µg/µl, drop volume: 0.6 µl, drying period: 2 h), which contained the polynucleotide sequence A in denatured form. The thin dash-dot curve in FIG. 9, however, depicts the course of $S_{21}$ for a coating consisting of a dried-out sample which contained the polynucleotide sequence A in hybridised form. The differences between the two curves can be clearly recognised. In order to characterise the differences, for example, the displacement $\Delta v$ of the transmission maximum or the modification $\Delta T$ of the value of the transmission maximum can be used. Compared to the uncoated resonator the example shows the following results:
 1. for the sample which contained the polynucleotide sequence pcDNA3 to be proven in denatured form: $\Delta v = -45$ GHz, $\Delta T = -9$ dB, and
 2. for the sample which contained the polynucleotide sequence pcDNA3 to be proven in hybridised form: $\Delta v = -120$ GHz, $\Delta T = -12$ dB.

The displacement and the change of the value of the transmission maximum of the resonator are correlated directly with complex index of refraction of the samples which were applied to the resonator. Hence the two parameters are to be understood as parameters equivalent to the components of the complex index of refraction of sample 1 which is in contact with the test medium 4 within the meaning of the Main Claim.

The state of linkage of a polynucleotide sequence B (hybridised vs. denatured) applied to the resonator can, therefore, be determined, for example, by means of the parameters $\Delta v$ and $\Delta T$ of the resonator. On the basis of these parameters it can be differentiated whether sample 1 contained or did not contain the polynucleotide sequence to be proven.

In general, a wave-guide arrangement, in particular one comprising sensitivity-increasing frequency-related structures, i.e. filters or resonators, will allow to achieve a higher detection sensitivity than a free-ray arrangement will do. The wave-guide arrangement is therefore particularly applicable for the execution of the method according to the invention in the scope of a medical laboratory.

It is finally stated that the embodiments presented herein are based on the generation of THz radiation by means of a femtosecond laser system. In view of future progress, in particular with respect to the semiconductor technology, it can be expected, however, that in the near future efficient sources for THz radiation in the relevant frequency range will be available, which will enable a commercial exploitation of the method.

Of course the method according to the invention can be applied to polynucleotide sequences of (practically) any length, in particular so to short-chain polynucleotide sequences with less than 20 base (pairs), often referred to as oligonucleotide sequences in the relevant literature.

| Literature list: | |
|---|---|
| [Katzenellenbogen 92] | N. Katzenellenbogen et al., in: Betroni (Ed.), Ultra-Wideband, Short Wavelength Electromagnetics, Plenum, N.Y. 1992 |
| [Wittlin 95] | A. Wittlin et al., Phys. Rev. A 34 (1986) 493 |
| [Cai 98] | Y. Cai et al., Appl. Phy. Lett. 72 (1998) 444 |
| [Smith 88] | P. R. Smith, D. H. Auston and M. C. Nuss, IEEE J. Quantum Electron. 24, 255, 1988. |
| [Nuss 98] | M. C. Nuss and J. Orenstein, "THz time-domain spectroscopy" in Millimeter and Sub-Millimeter Waves, ed. by G. Gruener (Springer-Verlag, Heidelberg, 1998). |
| [Haring 99] | P. Haring Bolivar, "Coherent THz spectroscopy", in Semiconductor Quantum Optoelectronics: |

| -continued | |
|---|---|
| Literature list: | |
| | From Quantum Physics to Smart Devices ed. by A. Miller, M. Ebrahimzahdeh and D. M. Finlayson, ISBN 0-7503-0628-9, (Institute of Physics Publishing, Bristol, 1999), pp. 151–192. |
| [Dahl 98] | C. Dahl, P. Goy and J. Kotthaus, "Magneto-optical millimeter-wave spectroscopy" in Millimeter and Sub-Millimeter Waves, ed. by G. Gruener (Springer-Verlag, Heidelberg, 1998). |
| [Saxena 89] | V. K. Saxena and L. L. Van Zandt, Phys. Rev. A 40, 6134 (1989). |
| [Zhuang 90] | W. Zhuang, Y. Feng, E. W. Prohofsky, Phys. Rev. A 41, 7033 (1990) |
| [Markelz 00] | A. G. Markelz, A. Roitberg, E. J. Heilweil, Chem. Phys. Lett. 320, 42 (2000) |
| [Smith 88] | P. R. Smith, D. H. Auston and M. C. Nuss, IEEE J. Quantum Electron. QE 24, 255, 1988. |

The invention claimed is:

1. A method of evidencing the presence of a polynucleotide sequence A in a sample containing a plurality of identical or different polynucleotide sequences X in the form of individual strands, where said polynucleotide sequence A may be identical to one of the polynucleotide sequences X or contained in one of the polynucleotide sequences X in the form of a sequence portion, by determining the binding status of the polynucleotide sequences X contained in the sample from a known test polynucleotide sequence B, which is complementary to the polynucleotide sequence A, said method comprising steps of:
 a) preparing a test medium which contains, in the form of individual strands, test polynucleotide sequences B which are complementary to the polynucleotide sequence A to be evidenced;
 b) bringing the sample into contact with said test medium by introducing the sample into, or applying it on, said test medium, so as to allow the individual strands of the polynucleotide sequences X contained in the sample to bind to the complementary test polynucleotide sequences B contained in said test medium;
 c) for evidencing the binding of polynucleotide sequences X to test polynucleotide sequences B, checking whether, in the frequency range from between 0.1 terahertz (THz) and 20 THz, contacting the sample with the test medium in accordance with step b) has caused a change to occur in at least one component of the complex index of refraction or an equivalent variable of the sample that is correlated with the formation of double-stranded polynucleotide sequences from the single-stranded polynucleotide sequences X and the single-stranded complementary test polynucleotide sequences B contained in said test medium.

2. The method as set forth in claim 1, wherein the checking of step c) is carried out using Terahertz Spectroscopy (TS).

3. The method as set forth in claim 2, wherein the Terahertz radiation used is pulsed ("pulsed Terahertz Spectroscopy" PTS), the pulses having a pulse duration ranging between 0.05 picoseconds (ps) and 10 Ps and being detected by a time resolved technique.

4. The method as set forth in claim 3, wherein the terahertz radiation used is detected by a frequency-resolved technique.

5. The method as set forth in claim 1, wherein the presence of a plurality N of different polynucleotide sequences A(1), . . . , A(N) is to be evidenced in the sample, a plurality N of test media each of which contains a test polynucleotide sequence B(1), ..., B(N) that is complementary to the polynucleotide sequences A(1), ..., A(N) to be evidenced being prepared for this purpose, said test media being fixed onto or in a substrate at different locations and the method steps b) and c) being carried out for every single one of the test media connected with the sample.

6. A device for carrying out the method as set forth in claim 1, said device comprising:
   a. a terahertz source for electromagnetic radiation;
   b. a wave guide structure along which the electromagnetic radiation generated by the terahertz source is allowed to propagate, the test medium containing the complementary polynucleotide sequences B being applied to a surface of the wave guide structure; and
   c. a terahertz detector for detecting the electromagnetic radiation transmitted along the wave guide structure or scattered by the sample.

7. The device as set forth in claim 6, wherein the wave guide structure includes a frequency-selective element that is disposed in the region of the test medium applied and locally increases the field intensity of the terahertz radiation.

8. A device for carrying out the method as set forth in claim 1, said device comprising:
   a. a terahertz source for electromagnetic radiation;
   b. a terahertz detector for detecting the electromagnetic radiation transmitted through the sample contacting the test medium or reflected or scattered by the sample; and
   c. a means for guiding the beam that is provided for guiding the electromagnetic radiation transmitted through the sample or reflected or scattered by the sample to the terahertz detector,
   wherein the terahertz source is configured to be a terahertz near field emitter.

9. A device for carrying out the method as set forth in claim 1, said device comprising:
   a. a terahertz source for electromagnetic radiation; b. a means for guiding the beam that is provided for guiding the electromagnetic radiation generated by the terahertz source to the sample contacting the test medium; and
   c. a terahertz detector for detecting the electromagnetic radiation transmitted through the sample or reflected or scattered by the sample,
   wherein the terahertz source is configured to be a terahertz near field detector.

* * * * *